United States Patent [19]

Kaper et al.

[11] Patent Number: 4,780,149

[45] Date of Patent: Oct. 25, 1988

[54] METHOD OF MAKING AND APPLYING BETA-LIMIT DEXTRIN CONTAINING STARCH HYDROLYSATES

[75] Inventors: Frederik S. Kaper, Blijham; Jan Aten, Wildervank; Meindert A. Reinders; Pieter Dijkstra, both of Veendam; Adolf J. Suvee, Ter Apel, all of Netherlands

[73] Assignee: Cooperatieve Verkoop- en Productievereniging van Aardappelmeel en Derivaten "AVEBE" B.A., Veendam, Netherlands

[21] Appl. No.: 36,786

[22] Filed: Apr. 10, 1987

[30] Foreign Application Priority Data

Apr. 14, 1986 [NL] Netherlands .......................... 8600937

[51] Int. Cl.[4] .......................... C13K 1/06; C12N 11/18; C12P 19/22
[52] U.S. Cl. ........................................ 127/38; 127/40; 127/65; 435/95; 435/99; 435/175
[58] Field of Search ............... 127/40, 38, 65; 435/95, 435/99, 175

[56] References Cited

U.S. PATENT DOCUMENTS 3,804,715  4/1974  Sugimoto et al. .................... 435/95
3,998,696  12/1976  Yomoto et al. ........................ 435/99

OTHER PUBLICATIONS

Swinkels, "Composition and Properties of Commercial Native Starches", Starch/Starke, 37, (1985), No. 1, pp. 1-3 and 5.

Primary Examiner—Curtis R. Davis
Assistant Examiner—Chung K. Pak
Attorney, Agent, or Firm—Mark T. Basseches; Paula T. Basseches

[57] ABSTRACT

A method of making beta-limit dextrin containing starch products is disclosed. The method comprises first treating fully or partially gelatinized starch with beta-amylase until a DE of 5-30 is reached, thereafter completely gelatinizing the resulting product as far as necessary and treating the resulting solution with alpha-amylase for a short period of time so that, as a result of the treatment with alpha-amylase, the DE of the starch hydrolysate is increased by no more than 3 units.

3 Claims, No Drawings

METHOD OF MAKING AND APPLYING BETA-LIMIT DEXTRIN CONTAINING STARCH HYDROLYSATES

This invention relates to a method of making and applying beta-limit dextrin containing starch products, and to the application of the products made in foods and pharmaceuticals.

In the depolymerization of dissolved starch with beta-amylase, 1,4-glucosidic bonds are broken from the non-reducing terminal groups of the starch molecules, whereby maltose is split off. When a branch point (1,6-glucosidic bond) or a modified glucose unit (e.g. phosphorylated or oxidized) is approached, the hydrolysis by the beta-amylase is terminated. In the case of amylopectin, this will commonly be the case at a 1,6-glucosidic bond (branch point), leaving an amylopectin molecule virtually stripped of its side chains. Such molecules and their products of hydrolysis with an average degree of polymerization in excess of 100 are referred to hereinafter as beta-limit dextrin. Amylose consists of unbranched and/or little branched chains and, in molecular dissolved form, is converted virtually completely into maltose by beta-amylase. Owing to the action of beta-amylase on starch, there is thus obtained a starch hydrolysate which consists as to 40–80% by weight of beta-limit dextrin and as to 20–60% by weight of maltose.

As early as 1814 Kirchhoff described a process in which gelatinized potato starch was treated with malt (contains beta-amylase). The result was a mixture of maltose and beta-limit dextrin. Thereafter, corresponding methods have been described in many publications. Up to now, however, subtantial industrial production of beta-limit dextrin containing starch hydrolysates has not come about.

It is an object of the present invention to provide an improved process for the manufacture of beta-limit dextrin containing starch hydrolysates. It is another object of the present invention to provide a process for the use of beta-limit dextrin containing starch hydrolysates in foods and pharmaceuticals.

The method according to the invention is characterized by treating fully or partially gelatinized starch first with a purified beta-amylase until a DE (dextrose-equivalent) of 10–30 is reached, whereafter the resulting product, as far as necessary, is completely gelatinized and the solution treated for a short time with alpha-amylase so that owing to the treatment with alpha-amylase, the DE of the starch hydrolysate is increased by no more than 3 DE units.

There are considerable differences in composition and properties between the various commercial starches. This has been described by J. J. M. Swinkels in Starch/Stärke, 37 (1985), Nr.1, pp. 1–5. In principle, all starches can be used for the method according to the present invention. The most suitable starches, however, are potato starch, tapioca starch and the waxy starches (for example, waxy corn starch).

Before the action of beta-amylase on the starch molecules, the starch granules must first be fully or partially gelatinized. In one embodiment of the invention, an aqueous starch suspension is heated until the viscosity is incrased from initial gelatinization. The beta-amylase is caused to act on the suspension of swollen starch granules under such conditions (time, temperature) that the granular form of the starch is largely maintained. During the hydrolysis, a portion of the starch molecules (in particular the amylose molecules) is dissolved from the swollen granules and is therefore decomposed by the beta-amylase to form, maltose. In another embodiment of the method according to the invention, the starch is first fully gelatinized in water, whereby the granular structure is totally lost. This can be effected, for example, by means of a steam injection apparatus (jet cooker) at 100°–200° C. After cooling the resulting starch solution to, for example, 80°–50° C., beta-amylase is added.

The starch concentration before the hydrolysis with beta-amylase is preferably 10–40% by weight. The beta-amylase compositions used must be purified so that, in particular, there is substantial absence of alpha-amylase activity and glucoamylase activity. Examples of suitable compositions are beta-amylase compositions isolated from soya and beta-amylase compositions isolated from certain bacteria. The beta-amylase is caused to act on the starch at a temperature of preferably 55°–70° C. Hydrolysis is continued until a DE of 5–30, and preferably of 10–25, is reached. If necessary (in case the hydrolysis was carried out with swollen granules), after the hydrolysis with beta-amylase, the starch granules are completely gelatinized by means, for example, of a jet cooker. Instead of beta-amylase, other exo-amylases can be used, such as glycoamylase and phosphorylase, and those isolated from the bacteria *Pseudomonas stutzeri* and *Aerobacter aerogenes*.

The starch hydrolysate solution obtained after the treatment with beta-amylase is subsequently treated with an alpha-amylase composition for a short time. As a result, the viscosity of the solution is considerably decreased. Preferably, the duration of the treatment is about 1–15. The degree of action on the alpha-amylase is determinative of the degree of polymerization of the resulting beta-limit dextrin. The treatment with alpha-amylase is carried out in such a manner that, as a result of the action of the alpha-amylase, the DE value of the hydrolysate is increased by no more than 3 DE units, and preferably by no more than 2 DE units. Subsequently, the hydrolysis by alpha-amylase is stopped by deactivating the enzyme (by reducing the pH or heating).

After stopping the alpha-amylase, the resulting solution can be converted, for example, by spray drying, into a dried starch hydrolysate with a DE of, for example, 5–30, which can be used as such.

In another embodiment of the method according to the invention, after stopping the alpha-amylase, beta-amylase is again added to the hydrolysate. Owing to the action of the beta-amylase, the maltose content rises further, as a result of which the DE of the hydrolysate is increased to, for example, DE 30–45. In this second action period, too, we preferably use purified beta-amylase at a temperature of 55°–70° C. The hydrolysate then obtained can be purified, for example, by filtration. The resulting solution can be converted, for example, by spray drying, into a dried starch hydrolysate consisting as to 30–50% by weight of beta-limit dextrin and as to 50–70% by weight of maltose. Owing to the presence of the high molecular beta-limit dextrins, spray drying can be satisfactorily accomplished in spite of the presence of a high maltose concentration. It is also possible, however, to convert the resulting solution into one product consisting substantially of beta-limit dextrin and another product consisting virtually exclusively of maltose, by means of ultrafiltration, activated carbon, ion exchangers, organic solvents, or dialysis.

In a further embodiment of the method according to the invention, after stopping the alpha-amylase, a precipitate is caused to form in the solution, which for the most part (more than 50% by weight) consists of amylase. The formulation of the precipitate is promoted by decreasing the temperature of the solution. The precipitate can be separated from the solution, for example, by filtration, decanting, or centrifugation. The resulting amylose-rich material is suitable as a filler and binder in tablets, and as a gelatin substitute in confections and capsules. The amylose material can also be used in packaging materials (amylose film) as a coating on fruit, foods and pharmaceuticals, in noodles and other doughs, as a sizing agent for glass fibers and other fibers, as a complexing agent for various substances, and as a gelating agent in foods, pharmaceuticals and cosmetics. Furthermore, the resulting amylose-rich material is suitable as a component in tablets, capsules and the like for the sustained release of active materials. The remaining liquid phase is a solution of beta-limit dextrin and maltose and can be dried as such. It is also possible, however, by ultrafiltration etc. to isolate the individual components, i.e. beta-limit dextrin and maltose, from the solution.

The mixture of beta-limit dextrin and maltose described hereinbefore and the beta-limit dextrin fraction isolated therefrom can be used in various foods and pharmaceutical products. Examples are confections with a gum structure (gums, liquorice and the like), extruded confections, soft drinks (stabilizer), bakery products (cake and the like), viscous dairy products (puddings and custards), coatings, deep-freeze products and tablets. Beta-limit dextrins can also be used as a carrier of dried liquids, such as fruit juices, soups, sauces, milk beverages, etc. When used in confections, the mixture of beta-limit dextrin with maltose functions both as a binder (beta-limit dextrin) and as a sweetener (maltose).

The invention is illustrated in and by the following examples.

EXAMPLE 1

To a suspension of potato starch in water (20% by weight of solids) 0.3% (by weight, calculated on solids content) of a beta-amylase composition, isolated from soya and purified was added. Subsequently the stirred suspension was heated to 60° C. Thereafter the suspension was slowly warmed up to 65° C. during 4 hours. During this period, the granular form was retained and the DE of the mixture increased to 18. Subsequently the suspension was pumped to a jet cooker, in which the suspension was gelatinized with steam at 140° C. After cooling to 80° C. 0.1% (by weight, calculated on dry matter) of an alpha-amylase composition (isolated from *Bacillus subtilis*) was added to the solution. After an alpha-amylase period of 5 minutes, the reaction was stopped by decreasing the pH to 2.5. The DE was then 19. Subsequently the hydrolysate was neutralized with soda to a pH of 4.8. Thereafter, 0.1% (by weight, calculated on dry matter) of the above beta-amylasae composition was added, which was allowed to act at 65° C. for 3 hours. Thereby a DE of 40 was obtained. Finally, the hydrolysate was filtered and spray dried. The resulting product consisted of a mixture of 44% by weight (calculated on the dry matter) of beta-limit dextrin, 44.5% by weight of maltose and 1.5% by weight of maltotriose.

EXAMPLE 2

A potato starch suspension (20% by weight of dry matter; pH 6.0) was gelatinized in a jet cooker at 155° C. After cooling to 65° C., 0.1% (by weight, calculated on dry matter) of a beta-amylase composition, isolated from soya was added to the starch solution. The beta-amylase was allowed to act at 65° C. for 2 hours, whereby a DE of 23 was attained. Subsequently, the hydrolysate was heated to 100° C., whereafter 0.05% (by weight, calculated on dry matter) of an alpha-amylase composition (isolated from *Bacillus licheniformis*) was added. After an action period of 3 minutes, the alpha-amylase was deactivated by decreasing the pH to 2.5. The DE of the hydrolysate was then 24. Subsequently, the pH was adjusted to 4.8 with soda, whereafter 0.1% (by weight, calculated on dry matter) of the above beta-amylase composition was added. The beta-amylase was allowed to act for 3 hours at 63° C., whereby a DE of 32 was reached. Finally, the solution was filtered and spray dried. The dried starch hydrolysate contained 49% by weight (calculated on dry matter) of beta-limit dextrin, 50% by weight of maltose and 1% by weight of maltotriose.

EXAMPLE 3

A suspension of waxy corn starch in water (23 parts by weight of dry matter; pH 6.7) was heated in a jet cooker to 160° C. After cooling to 65° C. and pH adjustment to 5.8, 0.075% (by weight, calculated on starch solids) of a beta-amylase composition isolated from soya was added to the resulting starch solution. After a reaction period of 2 hours, the DE was 20. The beta-amylase was then deactivated by reducing the pH to 2.7. After pH adjustment to 4.8, 0.004% (by weight, calculated on starch solids) of alpha-amylase (Optiamyl L 480) was added at 50° C. After 30 minutes, the DE was 22, and the alpha-amylase was stopped by adjusting the pH to 2.7. After separation of the insolubles, a clear stable solution was formed. Calculated on the solids content, the end product contained 34% of maltose and 66% of beta-limit dextrin, by weight.

EXAMPLE 4

A potato starch suspension (22% by weight of solids; pH 5.5) was converted into a starch solution by means of a jet cooker at 160° C. After cooling to 70° C., 0.1% (by weight, calculated on dry matter) of a beta-amylase composition isolated from soya was added. The beta-amylase was allowed to react at 65° C. for 1.5 hours, whereby a DE of 17 was reached. After deactivating the beta-amylase and cooling to 50° C., 0.05% (by weight, calculated on solids) of alpha-amylase was allowed to act on the mass for 10 mintues, whereby a DE of 18 was reached. Subsequently, the alpha-amylase was deactivated by reducing the pH to 2.5. Thereafter, the hydrolysate was allowed to stand at 40° C. for 18 hours. A precipitate was formed, which consisted as to 89% by weight of amylose. By filtration, the amylose precipitate was separated from the solution. The dried precipitate contained 20% of the weight of the starting material in potato starch (on solids basis). The filtrate was clear and consisted as to 50% by weight (calculated on dry matter and on the potato starch) of beta-limit dextrin and as to 30% by weight (calculated on the dry matter and on the potato starch) of maltose. By ultrafiltration the filtrate was split into one fraction rich in beta-limit dextrin and another fraction rich in maltose.

EXAMPLE 5

This example illustrates the use of the spray dried product obtained according to Example 1 as a combined binder (beta-limit dextrin component) and sweetener (maltose component) in the manufacture of gum-like confections (clear gums).

In a steam-heated kettle with a high-rate stirrer, 70.5 parts by weight of the spray dried mixture of beta-limit dextrin and maltose (obtained in accordance with Example 1) and 28.5 parts by weight of water were homogeneously mixed at a temperature of 70°-80° C. The mixed product was then passed to a jet cooker at 130° C. Thereafter 1 part by weight of citric acid and also colours and flavours were added to the resulting solution. Subsequently the solution was cast into moulds at 70° C. and dried at 60° C. for 24 hours. The end products had a good gum-like structure (as regards elasticity and chewability) and the desired clarity.

EXAMPLE 6

A mixture was made of 83.3 parts by weight of the combination of beta-limit dextrin and maltose (obtained according to Example 2); 1 part by weight of sal-ammoniac; 0.06 part by weight of aniseed oil; 0.48 part by weight of caramel; 0.13 part by weight of glycerolmonostearate and 7.3 parts by weight of water. This mixture was continuously supplied to an extruder and extruded at 75°-100° C. (Brabender extruder). After cooling, an elastic liquorice product of good gum structure was obtained.

What we claim:

1. A method of making beta-limit dextrin containing starch hydrolysate, characterized by first treating gelatinized starch with beta-amylase until a dextrose equivalent of 5-30 is reached and treating the resulting beta-amylase treated product with alpha-amylase, after deactivating said beta-amylase, until the resulting dextrose equivalent of the starch hydrolysate is increased by no more than 3 units.

2. A method as claimed in claim 1, further characterized by drying the starch hydrolysate recovered from the alpha-amylase treatment step.

3. A method as claimed in claim 1, further characterized in that, after the treatment with said alpha-amylase, the temperature of the starch hydrolysate is decreased until a separable amylose-rich precipitate is formed, and said precipitate is subsequently separated.

* * * * *